United States Patent [19]

Mahan et al.

[11] 3,956,411

[45] May 11, 1976

[54] ALKYLATION OF VINYLIDENE CHLORIDE AND VINYLIDENE BROMIDE

[75] Inventors: John E. Mahan; John R. Norell, both of Bartlesville, Okla.

[73] Assignee: Phillips Petroleum Company, Bartlesville, Okla.

[22] Filed: Aug. 8, 1974

[21] Appl. No.: 495,799

[52] U.S. Cl. .......................... 260/648 R; 260/654 R
[51] Int. Cl.² ................. C07C 17/26; C07C 21/04; C07C 21/02; C07C 25/18
[58] Field of Search ........ 260/648 R, 654 R, 683.47

[56] References Cited
UNITED STATES PATENTS

| | | | |
|---|---|---|---|
| 2,481,159 | 9/1949 | Schmerling | 260/648 R |
| 3,708,553 | 1/1973 | Olah | 260/683.47 |
| 3,778,489 | 12/1973 | Parker et al. | 260/683.47 |

*Primary Examiner*—D. Horwitz

[57] ABSTRACT

Vinylidene chloride and vinylidene bromide are alkylated by reaction with alkylating agents such as selected olefins, tert-alkyl halides, and secondary or tertiary alcohols in a reaction medium comprising trifluoromethane-sulfonic acid. In specific embodiments, the reaction medium can additionally comprise water, methanol, and $BF_3$.

12 Claims, No Drawings

ALKYLATION OF VINYLIDENE CHLORIDE AND VINYLIDENE BROMIDE

This invention relates to the production of alkylated 1,1-dichloro- and 1,1-dibromoolefins and to novel products produced. In accordance with another aspect, this invention relates to the production of alkylated vinylidene chloride or vinylidene bromide by the reaction of 1,1-dichloro- or 1,1-dibromoethylene with a selected alkylating agent in a reaction medium comprising trifluoromethanesulfonic acid. In accordance with another aspect, this invention relates to the alkylaton of vinylidene chloride and vinylidene bromide by reacting same with a selected alkylating agent in a reaction medium comprising trifluoromethanesulfonic acid including aqueous trifluoromethanesulfonic acid and alcoholic trifluoromethanesulfonic acid as well as one of these also containing $BF_3$. In accordance with a further aspect, this invention relates to the production of alkylated ethylenes by the reaction of vinylidene chloride or vinylidene bromide with a selected olefin, tert-alkyl halide, or secondary or tertiary alcohol in a reaction medium comprising trifluoromethanesulfonic acid.

The reaction of a vinylidene halide such as vinylidene chloride with selected alkylating agents in a $BF_3$-aqueous sulfuric acid catalyst-solvent system which yields substituted acetic acids is known as the Bott Carboxylic Acid Synthesis. The alkylating agent can be derived from an olefin, secondary or tertiary alcohol, or a tert-alkyl halide. We have found that reaction of vinylidene halides such as vinylidene chloride or vinylidene bromide with alkylating agents such as selected olefins, tert-alkyl halides, and secondary or tertiary alcohols in the presence of trifluoromethanesulfonic acid leads not to the Bott-type acid, but rather to 1,1-dichloro- or 1,1-dibromo-2-alkyl(or cycloalkyl)ethylenes.

Accordingly, an object of this invention is to provide a new process for the production of alkylated 1,1-dichloro- or 1,1-dibromoolefins.

Another object of this invention is to provide an effective reaction medium which substantially increases the yield of the desired alkylated 1,1-dichloro- or 1,1-dibromoolefins.

A further object of this invention is to provide novel alkylated vinylidene chlorides or vinylidene bromides.

A still further object of this invention is to provide a process for the production of alkylated vinylidene chlorides or vinylidene bromides.

Another object of this invention is to provide an improved process for the production of alkylated vinylidene chlorides or vinylidene bromides at low cost and in high yields.

Other objects and aspects, as well as the several advantages of the invention, will be apparent to those skilled in the art upon reading the specification and the appended claims.

In accordance with the invention, alkylated 1,1-dichloroethylenes or 1,1-dibromoethylenes are prepared by the reaction of selected alkylating agents with vinylidene chloride or vinylidene bromide in a reaction medium comprising trifluoromethanesulfonic acid.

In accordance with another embodiment of the invention, a process is provided for the production of alkylated vinylidene chlorides or vinylidene bromides which comprises reacting at least one of vinylidene chloride or vinylidene bromide with at least one alkylating agent in a reaction medium comprising trifluoromethanesulfonic acid.

In accordance with a further embodiment of the invention, alkylated vinylidene chlorides or vinylidene bromides are produced by the reaction of vinylidene chloride or vinylidene bromide with at least one alkylating agent selected from suitable olefins, tert-alkyl halides, or secondary and tertiary alcohols in a reaction medium comprising trifluoromethanesulfonic acid.

In accordance with a still further embodiment of the invention, the reaction medium can comprise trifluoromethanesulfonic acid ($CF_3SO_3H$) alone or aqueous trifluoromethanesulfonic acid or alcoholic trifluoromethanesulfonic acid, or any one of the preceding which contains $BF_3$.

Olefins which are suitable alkylating agents for use in the present invention are described by the formula:

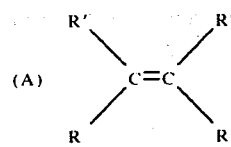

(A)

wherein the total number of carbon atoms is 4 to 20, R and R' represent hydrogen or alkyl containing 1 to 12 carbon atoms with the proviso that R is hydrogen if two R' groups together represent an alkylene group containing 3 to 6 carbon atoms, or a cycloalkylene group containing 5 or 6 carbon atoms, or an alkenylene group containing 6 carbon atoms.

Illustrative olefins having the formula as described above that can be used according to the invention include norbornene, 1,5-cyclooctadiene, isobutylene, cyclohexene, cyclopentene, 2-methylbutene-2, 2-methylhexene-2, pentene-2, 4-methylpentene-2, octene-2, heptene-3, 5-ethyloctadecene-5, pentene-1, tridecene-1, and the like. If desired, mixture of the olefins can be used.

Tertiary alcohols which are suitable alkylating agents are described by the formula:

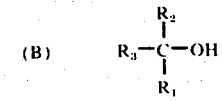

(B)

wherein the total number of carbon atoms is 4 to 20, and $R_1$, $R_2$, and $R_3$ can be the same or different and represent alkyl containing 1 to 12 carbon atoms.

Examples of tertiary alcohols described by the above formula that can be used as alkylating agents according to the invention include tert-butanol, 5-n-propylheptadecan-5-ol, 2-methylbutan-2-ol, 2-methylnonan-2-ol, 3-methylheptan-3-ol, 2-methylhexan-2-ol, 3-ethylpentan-3-ol, and the like. If desired, mixtures of the tertiary alcohols can be used.

Secondary alcohols which are suitable alkylating agents according to the invention are described by the formula:

(C) 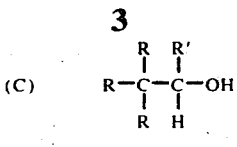

wherein the total number of carbon atoms is 4 to 20, R represents hydrogen or alkyl, and R' represents alkyl, said alkyls containing 1 to 12 carbon atoms with the proviso that R' and one R group together can represent an alkylene group containing 3 to 8 carbon atoms, cycloalkylene group containing 5 or 6 carbon atoms or an alkenylene group containing 6 or 7 carbon atoms.

Examples of secondary alcohols having the above formula that can be used according to the invention include norborneol, cyclopentanol, cyclohexanol, cyclooctanol, 3-n-butylhexadecan-2-ol, 5-hydroxy-1-cyclooctene, 2-butanol, 3-heptanol, cyclodecanol, and the like. Mixtures of the secondary alcohols can be used if desired.

Tertiary alkyl halides which are suitable alkylating agents are described by the formula:

(D) 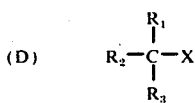

wherein X is bromine or chlorine and the total number of carbon atoms is 4 to 20, and $R_1$, $R_2$, and $R_3$ can be the same or different and represent alkyl containing 1 to 12 carbon atoms.

Examples of suitable tertiary alkyl halides include tert-butyl chloride, tert-butyl bromide, 3-chloro-3-ethylpentane, 2-bromo-2-methylhexane, 3-chloro-3-methylnonane, 5-n-propyl-5-bromoheptadecane, 2-methyl-2-chlorobutane, 2-methyl-2-bromononane, 3-methyl-3-chloroheptane, 3-methyl-3-chlorononane, 2-methyl-2-bromohexane, 3-ethyl-3-chloropentane, and the like. Mixtures of these compounds can be used if desired.

The reaction will be carried out at a temperature sufficient to cause a reaction between the vinylidene chloride or vinylidene bromide and the alkylating agent. Similarly, the reaction time and molar ratio of various reactants are such as to cause a reaction for the production of alkylated vinylidene chloride or alkylated vinylidene bromide.

The reaction generally will be carried out at a temperature in the range of −40°C to 50°C, preferably −20°C to 30°C, with the reaction time generally varying from 15 minutes to 48 hours, more often varying from 30 minutes to three hours.

The molar ratio of vinylidene chloride or vinylidene bromide to alkylating agent will generally be in the range of 0.3:1 to 10:1, more often 0.9:1 to 3:1. The molar ratio of trifluoromethanesulfonic acid to alkylating agent will generally be in the range of 0.5:1 to 10:1, more often 0.8:1 to 3:1.

As indicated above, the reaction medium can comprise trifluoromethanesulfonic acid alone or aqueous trifluoromethanesulfonic acid or methanoltrifluoromethanesulfonic acid or any one of the three reaction media containing $BF_3$. The weight percent of $BF_3$, based on trifluoromethanesulfonic acid, or based on the weight of trifluoromethanesulfonic acid with water or methanol, and $BF_3$, generally ranges from 0 to 10 weight percent, more often 6 to 8 weight percent. The weight percent of water or methanol, based on the weight of trifluoromethanesulfonic acid and water or methanol, will range from 0 to 25 weight percent, more often 0 to 10 weight percent. As indicated by the specific working examples hereinbelow, $BF_3$ is not required as a component of the reaction medium to obtain a high yield of the desired alkylated vinylidene chloride or vinylidene bromide product.

The reaction can be carried out in the presence of a solvent such as, for example, liquid $SO_2$, 1,1,2-trichloro-1,2,2-trifluoroethane, chlorosulfurylfluoride ($SO_2ClF$), and the like.

The present process can be carried out in a continuous, semi-continuous, or batch manner with or without diluents. The alkylated vinylidene chloride or vinylidene bromide product produced according to the invention can be recovered from the reaction by well-known procedures including fractionation, crystallization, filtration, solvent extraction, and the like.

The alkylated vinylidene chlorides or vinylidene bromides produced according to the invention have utility as agricultural chemicals, i.e., pesticides and herbicides, as well as intermediates for the preparation of carboxylic acids. In addition to their utility as agricultural chemicals, the vinylidene bromide derivatives are useful as flame retardants.

The reactants can be brought together in any desirable order. However, it is preferable to add the alkylating agent and vinylidene chloride or vinylidene bromide to the trifluoromethanesulfonic acid reaction mixture.

The following examples serve to illustrate but in no way limit the practice of the present invention.

EXAMPLE I

To 30 ml (51.0 g, 0.34 mol) of trifluoromethanesulfonic acid was added a mixture of 37.0 g (0.50 mol) tert-butanol and 72.5 g (0.75 mol) vinylidene chloride at 0.5°C over a period of 1 hour. After stirring an additional 2 hours, the contents were poured on ice. After extraction with ether (3 × 100 ml), the extracts were washed twice with water, followed by a washing with 10 percent NaOH and two additional water washes. The ether extracts were dried over $MgSO_4$ and concentrated to 33.9 g of a dark residue. Distillation of 32.7 g of this concentrate gave a heart cut of 22.1 g (b.p. 42°-44°C at 20 mm, $n_D^{20}$ 1.4520) with 4.0 g of heavy residue. Acidification of the water extracts and extraction yielded only 0.3 g of acid.

Infrared and nuclear magnetic resonance spectral data verified that the major product was 1,1-dichloro-3,3-dimethylbutene-1, (tert-butyl-vinylidene chloride). This example illustrates the use of a tertiary alcohol as the alkylating agent in the presence of trifluoromethanesulfonic acid.

EXAMPLE II

A mixture of 17.5 g (0.25 mol) 2-methylbutene-2 and 36.2 g (0.37 mol) vinylidene chloride was added to 30 ml of a mixture containing approximately 8 weight percent $BF_3$, 9 weight percent water, and 83 weight percent trifluoromethanesulfonic acid. After stirring for 2 hours at 0°–20°C, the reaction mixture was worked up in essentially the same manner as described in Example I to give 32.9 g of a brown oil. Gas chromatographic analysis of the crude mixture indicated at least nine components with the desired product 1,1-dichloro-3,3-dimethylpentene-1 representing 63 percent of the mixture. Distillation presented difficulties due to excessive foaming and clean fractions were not obtained. Distillation of 32.0 g was as shown:

| Cut | Head, °C | Pot, °C | mm | Wt., g |
|---|---|---|---|---|
| 1 | foamed over | — | — | 1.13 |
| 2 | 55–68 | 70 | 30→27 | 11.62 |
| 3 | 68–70 | 80–93 | 28 | 4.90 |
| 4 | 70 | 93–103 | 28–16 | 2.48 |
| 5 | 70–78 | 103–111 | 16–14 | 1.15 |
| 6 | 78–73 | 111–110 | 14–5 | 0.73 |
| 7 | 73 | 110 | 5–0.2 | 2.30 |
|  | Residue |  |  | 5.08 |

The residue accounted for 16 percent of the still charge. Cut 2 contained 56.6 percent of 1,1-dichloro-3,3-dimethylpentene-1; Cut 3, 91.8 percent; and Cut 4, 81.6 percent. With Cut 2 an unknown component eluted 1.2 minutes earlier than the product and accounted for 43 percent of the cut. Based on the content of the above three cuts, the distilled yield of 1,1-dichloro-3,3-dimethylpentene-1 was 31 percent. The structure of the major product was verified by infrared and nuclear magnetic resonance spectral data. This example illustrates the use of 2-methylbutene-2 in the present process.

The $BF_3/CF_3SO_3H/H_2O$ (or $CH_3OH$) mixture was prepared by bubbling gaseous $BF_3$ into a solution containing 90 weight percent $CF_3SO_3H$ and 10 weight percent $H_2O$ (or $CH_3OH$). The $BF_3$ was added until the mixture contained approximately 8 weight percent $BF_3$ based on the total weight of $CF_3SO_3H + BF_3 + H_2O$ (or $CH_3OH$). The three-component mixture thus contained approximately 83 weight percent $CF_3SO_3H$, 9 weight percent $H_2O$ (or $CH_3OH$) and 8 weight percent $BF_3$.

EXAMPLE III

To 30 ml of a mixture containing approximately 8 weight percent $BF_3$, 9 weight percent water, and 83 weight percent trifluoromethanesulfonic acid, cooled to 0°C, was added a mixture of vinylidene chloride (36.2 g, 0.37 mol) and isobutylene (15.0 g, 0.27 mol). The mixture of isobutylene and vinylidene chloride was prepared by cooling the latter in ice and bubbling isobutylene into the solution until the desired weight was obtained. The mixture was transferred to a jacketed addition funnel with circulating ice water. Addition time was 20 minutes, after which the mixture was allowed to warm to 19°C while stirring for 2 hours. The contents were poured on ice, made basic with 10 percent NaOH, and ether extracted. After drying and concentration of the ether extracts, there was obtained 29.4 g of a dark residue. Gas chromatographic analysis indicated 80.5 percent of the volatile material was 1,1-dichloro-3,3-dimethylbutene-1 (tert-butylvinylidene chloride). Residual ether accounted for 9.1 percent, an unknown peak of 3.6 percent, and the remaining 6.8 percent was dispersed over 15 peaks. Acidification of the aqueous layer and extraction yielded a residue of 2.9 g; infrared spectral analysis indicated the presence of a minor amount of a carboxylic acid. Distillation of 28.1 g of the above oil proceeded as shown:

| Cut | Head, °C | Pot, °C | mm | Wt., g |
|---|---|---|---|---|
| 1 | 58–62 | 70–67 | 56–58 | 0.7 |
| 2 | 58–61 | 63–80 | 48 | 17.0 |
| 3 | 61 | 80–100 | 48 | 0.9 |
| 4 | 61–70 | 100–120 | 48→2 | 2.6 |
| 5 | 68 | 114–125 | 2→0.2 | 0.7 |

Cut 2 corresponds to a distilled yield of 41 percent (1,1-dichlor-3,3-dimethylbutene-1). (U.S. Pat. No. 2,481,159: b.p. 59–61 at 40 mm, $n_D^{20}$ 1.4535).

This example illustrates the use of isobutylene as the alkylating agent in the inventive process.

EXAMPLE IV

For comparative purposes, a run was made with sulfuric acid in place of trifluoromethanesulfonic acid ($CF_3SO_3H$) as described in Example III. A mixture of 15.0 g (0.25 mol) isobutylene and 36.2 g (0.37 mol) vinylidene chloride was added to 30 ml of a mixture containing approximately 8 weight percent $BF_3$, 9 weight percent $H_2O$, and 83 weight percent $H_2SO_4$. Workup of the reaction mixture in essentially the same manner as described in Example I gave an ether extract which on concentration gave 3.8 g of an orange oil containing mostly butylene oligomers. Acidification of the aqueous layer followed by extraction gave 20.1 g of a carboxylic acid. Distillation provided 14.6 g (b.p. 55°C at 1.0 mm) [Chem. Ber., 100, 978 (1967), b.p. 80°–82°C (12 mm)] of tert-butylacetic acid representing a 50 percent yield.

Infrared and nuclear magnetic resonance spectral data verified that the distilled product was tert-butylacetic acid. This example illustrates that the prior art process using aqueous $H_2SO_4$ containing $BF_3$ gives tert-butylacetic acid as the major product rather than 1,1-dichloro-3,3-dimethylbutene-1 in contrast to the inventive run of Example III.

EXAMPLE V

A mixture of pentene-1 (17.5 g, 0.25 mol) and vinylidene chloride (36.2 g, 0.37 mol) was added to 30 ml of a mixture containing approximately 8 weight percent $BF_3$, 83 weight percent trifluoromethanesulfonic acid, and 9 weight percent $H_2O$ at 0°C. After one hour addition time, the mixture was stirred an additional 2.5 hours. Workup as described in Example I provided 27.7 g of a green extract. Distillation of 27.4 g of this extract was as follows:

| Cut | Head, °C | Pot, °C | mm | Wt., g |
|---|---|---|---|---|
| 1 | 25–44 | 60–75 | 115 | 0.33 |
| 2 | 49–44 | 75–101 | 115 | 2.53 |
| 3 | 37–85 | 93 | 80–79 | 0.47 |
| 4 | 85–89 | 93–101 | 79–70 | 12.13 |
| 5 | 89–62 | 101–100 | 70–0.4 | 3.20 |
|  | Residue |  |  | 3.10 |
|  | Trap |  |  | 4.60 |

Cut 4 which was 96.1 area percent isomeric pentyl vinylidene chlorides by gas chromatographic analysis was redistilled to give a heart cut, b.p., 50.5°–51°C (9 mm). A sample of this material (99.1 area percent purity by glc analysis) gave the following elemental and molecular weight analysis:

Anal. Calc'd. for $C_7H_{12}Cl_2$: C, 50.32; H, 7.24; Cl, 42.44; M.W., 167. Found: C, 50.37; H, 7.37; Cl, 41.6; M.W., 167.

According to nuclear magnetic resonance analysis, the major product consisted principally of the following isomeric chlorides:

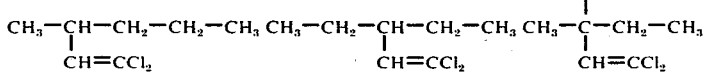
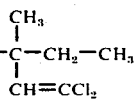

Example V illustrates the use of the present inventive process with a linear alpha-olefin feedstock.

EXAMPLE VI

A mixture of cyclohexene (20.5 g, 0.25 mol) and vinylidene chloride (36.2 g, 0.37 mol) was added to 30 ml of a mixture containing approximately 8 weight percent $BF_3$, 83 weight percent trifluoromethanesulfonic acid, and 9 weight percent methanol at 0°C. After stirring for 2 hours at 20°–23°C, the mixture was poured on ice, made basic with 10 percent NaOH and ether extracted. Concentration gave 41.3 g of an oil. Acidification followed by extraction of the aqueous layer gave 0.90 g of carboxylic acids. Gas chromatographic analysis of the oil indicated 1.7 percent cyclohexyl chloride, 6.4 percent 1,1-dichloro-2(1-methylcyclopentyl)ethylene, 85.6 percent of 2-cyclohexyl-1,1-dichloroethylene, 5.1 percent residual diethyl ether, and 1.1 percent cyclohexene. Distillation of 39.43 g of this oil provided essentially one cut, b.p. 78°–85°C (9–10 mm), giving 32.0 g (70 percent yield) of product with 4.6 g of a greenish residue. Gas chromatographic analysis of the distilled sample indicated 1.8 area percent of a low boiling peak, 7.0 area percent ring condensed material, and 91.2 area percent cyclohexylvinylidene chloride.

Example VI illustrates the use of a cyclic olefin feedstock such as cyclohexene in the present invention.

EXAMPLE VII

The reaction was run as described in Example VI except the reaction medium was trifluoromethanesulfonic acid. A crude product of 38.4 g was obtained which on distillation (b.p. 88°–89°C at 14 mm) gave 18.4 g of 2-cyclohexyl-1,1-dichloroethylene, 41 percent yield. There remained in the still pot 14.0 g of heavy residue (38 percent of charge).

Example VII illustrates that the present invention can be carried out in trifluoromethanesulfonic acid without the addition of $BF_3$ or $H_2O$ or $CH_3OH$.

EXAMPLE VIII

A mixture of cyclohexene (0.25 mol) and vinylidene chloride (0.37 mol) was added to a mixture of methanol (8.0 g, 0.25 mol) and 30 ml (51.0 g, 0.34 mol) trifluoromethanesulfonic acid at 0°C over a period of 1 hour. After stirring for 1.5 hours and warming to 20°C, the usual workup gave 23.2 g of a dark residue. Gas chromatographic analysis indicated 21.5 percent cyclohexyl methyl ether and 38.8 percent cyclohexylvinylidene chloride. Since the product was still acidic, it was treated with base to give 18.5 g of a red-brown oil. Gas chromatographic analysis of the red-brown oil was similar to that observed on the dark residue before base treatment. Distillation of 16.5 g was as shown:

| Cut | Head, °C | Pot, °C | mm | Wt., g |
|---|---|---|---|---|
| 1 | 32 | 68–95 | 13 | 0.63 |
| 2 | 32 | 95–100 | 13 | 0.25 |
| 3 | 55–89 | 105–106 | 13 | 0.47 |
| 4 | 89–95 | 106–125 | 13 | 3.21 |
| 5 | 95–105 | 124–143 | 13 | 1.36 |
| 6 | 105–110 | 143–210 | 13 | 1.08 |
|   |   | Residue |   | 7.11 |

Many peaks still remained in each cut with no cut possessing a high purity. Cut 4 contained 87.1 percent of the desired adduct, cyclohexylvinylidene chloride, and Cut 6 contained a heavier peak which was 74.8 percent of that cut. It appeared that decomposition occurred on distillation due to the presence of residual trifluoromethanesulfonate esters. This example illustrates the operability of the present inventive process in the presence of methanolic trifluoromethanesulfonic acid.

EXAMPLE IX

In a flame-dried 300 ml three-neck flask was condensed 100 ml of sulfur dioxide, 30 ml trifluoromethanesulfonic acid were added, followed by dropwise addition of a mixture of cyclohexene (0.25 mol) and vinylidene chloride (0.37 mol). The reaction was run for 3.5 hours at $-35°$ to $-15°C$. The contents were poured on water and made basic with 10 percent NaOH. The mixture was ether extracted, dried and concentrated to give 40.3 g of an oil. Distillation of 38.5 g of oil provided 28.0 g (65 percent yield) of 2-cyclohexyl-1,1-dichloroethylene as a colorless liquid, b.p. 55°–57°C (2.2 mm). Heavy residue amounted to 6.4 g (17 percent).

This example illustrates the use of liquid $SO_2$-$CF_3SO_3H$ as the reaction medium for the inventive process.

EXAMPLE X

A mixture of cyclohexene (0.25 mol) and vinylidene chloride (0.36 mol) was added to 30 ml of a mixture containing approximately 8 weight percent $BF_3$, 9 weight percent water, and 83 weight percent trifluoromethanesulfonic acid at 0°C. The mixture was stirred for 1.5 hours at 14°–20°C; then 75 ml of n-hexane was added. The dark solution was poured into a separatory funnel and the lower acid layer was returned to the reaction flask. The hexane layer was shaken with 10 percent NaOH and ether extracted. Drying and concentration of the organic phase provided 36.9 g of a yellow oil (A). Acifidication of the aqueous layer gave only 0.1 g of acidic residue.

To the initial lower acid layer separated from the preceding reaction mixture was added a fresh mixture of cyclohexene (0.25 mol) and vinylidene chloride (0.36 mol) and stirred for two hours at 18°–25°C. Hexane (200 ml) was added to the mixture and the product extracted. Concentration of the organic phase provided 19.5 g of a dark residue (B). Acidification of the water washes gave 0.1 g of acidic material.

The residual strong acid layer was poured on ice, made basic and extracted with ether. Drying and concentration of the ether extract provided 12.3 g of a residue (C). Acidification of the aqueous residue and extraction gave 1.8 g of acidic residue. Glc of the three crude mixtures was as follows:

| Glc Retention Time, min. | A | B | C | Area Percent Identification |
|---|---|---|---|---|
| 1.2 | 0.2 | 0.3 | 5.1 | — |
| 1.3 | 14.7 | 13.7 | 0.2 | — |
| 1.5 | 0.8 | 3.5 | 1.0 | — |
| 3.0 | 15.9 | 0.1 | 11.5 | Cyclohexanol |
| 4.3 | 0 | 2.7 | 75.5 | Cyclohexyl acetate |
| 6.1 | 7.6 | 1.7 | tr. | (1-Methylcyclopentyl)vinylidene chloride |
| 6.9 | 60.2 | 68.2 | 4.1 | Cyclohexylvinylidene chloride |
| 7.6 | tr. | 0.2 | tr. | — |
| 8.5 | tr. | 0.3 | 0.2 | — |
| 8.9 | tr. | 5.4 | 0.3 | — |
| 15–17 | 0.4 | 1.1 | 1.6 | — |

Based on gas chromatography (area percent), residues A, B, and C represented, respectively, 51.7, 30.9, and 1.2 percent yields of 2-cyclohexyl-1,1-dichloroethylene.

Example X shows that the inventive process can be carried out in a continuous manner.

EXAMPLE XI

A mixture of cyclopentene (0.25 mol, 17.0 g) and vinylidene chloride (0.37 mol, 36.2 g) was added to a mixture containing approximately 8 weight percent $BF_3$, 9 weight percent water, and 83 weight percent trifluoromethanesulfonic acid at 0°C over a period of 30 minutes. The mixture was stirred an additional two hours. On workup there was obtained 32.0 g of a green oil which by gas chromatographic analysis contained 80 percent of 1,1-dichloro-2-cyclopentylethylene. Distillation of 30.9 g of the green residue was as follows:

| Cut | Head, °C | Pot, °C | mm | Wt., g | $n_D^{20}$ |
|---|---|---|---|---|---|
| 1 | 33–43 | 58–69 | 14 | 0.35 | — |
| 2 | 43–72 | 69–77 | 11 | 0.40 | — |
| 3 | 72–72 | 77–110 | 11 | 22.0 | 1.4940 |
| 4 | 72–59 | 110–122 | 11 | 1.0 | — |
|   | Residue |   |   | 2.3 |   |
|   | Trap |   |   | 4.2 |   |

Cut 3 represents a 54 percent yield and was redistilled to give an analytical sample of 1,1-dichloro-2-cyclopentylethylene (cyclopentylvinylidene chloride).

Anal. Calc'd. for $C_{17}H_{10}Cl_2$: C, 50.94; H, 6.11; Cl, 42.95; M.W., 165. Found: C, 51.93; H, 6.19; Cl, 40.6; M.W., 165.

Infrared and nuclear magnetic resonance spectral data gave conclusive support for the 1,1-dichloro-2-cyclopentylethylene structure. Acidic materials amounted to 2.5 g.

Example XI describes the use of a cyclic olefin feedstock such as cyclopentene in the present inventive process.

EXAMPLE XII

A mixture of norbornene (23.5 g, 0.25 mol) and vinylidene chloride was added to a mixture containing approximately 8 weight percent $BF_3$, 9 weight percent water, and 83 weight percent trifluoromethanesulfonic acid at 0°C. After stirring at 20°C for 2 hours, the usual workup provided 42.1 g of product. Distillation gave 36.9 g (77 percent yield), b.p. 61°–63°C (0.7 mm) [Chem. Ber., 100, 978 (1967), b.p. 108°–110°C/20 mm] of 1,1-dichloro-2-norbornylethylene with only five percent heavy residue.

Example XII demonstrates the use of a bicyclic olefin feedstock such as norbornene in the inventive process.

EXAMPLE XIII

A mixture of 1,5-cyclooctadiene (27.0 g, 0.25 mol) and vinylidene chloride (36.2 g, 0.37 mol) was added dropwise to a mixture containing approximately 8 weight percent $BF_3$, 9 weight percent water, and 83 weight percent trifluoromethanesulfonic acid over a period of 1 hour at 0°–10°C. After stirring for 2 hours the mixture was poured on ice, made basic with 10 percent NaOH and extracted with ether. Drying and concentration of the ether extract provided 40.0 g of a green oil. Distillation of 37.4 g of this green oil was as shown:

| Cut | Head, °C | Pot, °C | mm | Wt., g | $n_D^{20}$ |
|---|---|---|---|---|---|
| 1 | 40–64 | 75–78 | 0.2 | 1.45 | — |
| 2 | 64–66 | 78–110 | 0.2 | 22.72 | 1.5174 |
| 3 | 66–70 | 110–130 | 0.2 | 1.22 | — |
|   | Residue |   |   | 9.51 | 1 |

Cut 2 corresponds to a yield of 44 percent of 1,1-dichloro-2-(1-bicyclo[3.3.0]-octyl)ethylene with a residue consisting of 25 percent of the still charge. Redistillation of Cut 2 (89°–90°C/2 mm) gave a pure sample for analysis.

Anal. Calcd. for $C_{10}H_{14}Cl_2$: C, 58.55; H, 6.88; Cl, 34.57; M.W., 205. Found: C, 58.62; H, 6.89; Cl, 34.0; M.W., 204.

Infrared and nuclear magnetic resonance analyses along with the elemental analysis verified that the structure of the major product was 1,1-dichloro-2-(1-bicyclo-[3.3.0]-octyl)ethylene. The compound 1,1-dichloro-2-(1-bicyclo-[3.3.0]-octyl)ethylene is a new composition of matter.

A summary of runs selected from the Examples I–XIII is given below in Table I.

TABLE I

ALKYLATION OF VINYLIDENE CHLORIDE WITH VARIOUS OLEFINS IN SYSTEMS CONTAINING TRIFLUOROMETHANESULFONIC ACID RCH=CCl$_2$

| Example No. | Olefin | Acid | Yield, %[a] glc | Distd. | Distn.[1] Residue | b.p. | mm | $n_n^{20}$ |
|---|---|---|---|---|---|---|---|---|
| I | d | CF$_3$SO$_3$H | 40 | 29 | 12 | 42–44 | 20 | 1.4520 |
| II | 2-Methyl-butene-2 | 8% BF$_3$ in 90% aq.CF$_3$SO$_3$H | 50 | 31 | 16 | 68–70 | 28 | N.D. |
| III | Isobutylene | 8% BF$_3$ in 90% aq. CF$_3$SO$_3$H | 57 | 41 | N.D. | 58–61 | 48 | N.D. |
| IV | Isobutylene | 8% BF$_3$ in 90% aq. H$_2$SO$_4$ | b | b | b | b | b | b |
| V | 1-Pentene | 8% BF$_3$ in 90% aq. CF$_3$SO$_3$H | 40 | 29 | 11 | 50–51 | 9 | N.D. |
| VI | Cyclohexene | 8% BF$_3$ in 10% MeOH— 90% CF$_3$SO$_3$H | 85 | 70 | 11 | 78–85 | 9–10 | N.D. |
| VII | Cyclohexene | CF$_3$SO$_3$H | 79 | 41 | 38 | 88–89 | 14 | |
| VIII | Cyclohexene | 10% CH$_3$OH 90% CF$_3$SO$_3$H | 87.1[c] | N.D. | 43 | N.D. | N.D. | N.D. |
| IX | Cyclohexene | CF$_3$SO$_3$H—SO$_2$ | | 65 | 17 | 55–57 | 2.2 | N.D. |
| X | Cyclohexene | 8% BF$_3$ in 90% aq. CF$_3$SO$_3$H | 51.7 | N.D. | N.D. | N.D. | N.D. | N.D. |
| XI | Cyclopentene | 8% BF$_3$ in 90% aq. CF$_3$SO$_3$H | 62 | 54 | 7 | 70–73 | 10–11 | 1.4940 |
| XII | Norbornene | 8% BF$_3$ in 90% aq. CF$_3$SO$_3$H | 85 | 77 | 5 | 61–63 | 0.7 | N.D. |
| XIII | 1,5-Cyclo-octadiene | 8% BF$_3$ in 90% aq. CF$_3$SO$_3$H | 63 | 44 | 25 | 64–66 | 0.2 | 1.5174 |

[1]Percent of still charge. N.D. represents not determined.
[2]Cyclohexyl chloride was obtained in 21 percent yield.
[a]The difference in the distilled ("Distd.") yield and the "glc" yield reflects the relative amount of heavies produced in the various runs.

[b]The major product was tert-butylacetic acid (b.p. 55°C/1.0 mm) which was obtained in 50% distilled yield.
[c]This was a low yield run and 87.1% represents the maximum concentration of the alkylated vinylidene chloride in one of the major fractions.
[d]Feedstock was tert-butyl alcohol.

EXAMPLE XIV

A run was carried out with the following charge: cyclohexene (10.7 g), vinylidene bromide (27.87 g), and 20 ml of a mixture containing approximately 8 weight percent BF$_3$, 9 weight percent CH$_3$OH, and 83 weight percent trifluoromethanesulfonic acid. Workup in the usual manner provided 32.1 g of a dark green oil. Distillation of this oil gave 17.33 g of cyclohexylvinylidene bromide (48.7% yield). The structure of the major product was verified by nuclear magnetic resonance spectral data and elemental analysis.

Anal. Calc'd. for C$_8$H$_{12}$Br$_2$: %C, 35.85; %H, 4.51. Found: %C, 36.44; %H, 4.60.

The compound, cyclohexylvinylidene bromide, is a novel composition of matter.

EXAMPLE XV

Three control runs were carried out with olefin alkylation outside the scope of the invention but with a reaction medium comprising trifluoromethanesulfonic acid according to the invention. In all three control runs substantially no alkylated vinylidene chloride product was observed.

In each control run the alkylating agent, either 1-methylcyclopentene or 4-vinylcyclohexene or 3-cyclohexene-1-carbonitrile (about 0.25 mol each), and vinylidene chloride (about 0.37 mol) were added to a reaction mixture comprising 8 weight percent BF$_3$, 9 weight percent water, and 83 weight percent trifluoromethanesulfonic acid. The reaction was carried out over a period of time at about 0°–10°C. Recovery and separation of the product resulted in substantially no alkylated vinylidene chloride.

In another control run norbornadiene, another olefin outside the scope of the invention, was used again in a reaction medium according to the invention. In this run norbornadiene and vinylidene chloride were added in about the same amounts as above to a reaction medium comprising approximately 8 weight percent BF$_3$, 83 weight percent trifluoromethanesulfonic acid, and 9 weight percent methanol. The reaction was carried out for an extended period under about the same conditions as set forth above for the other control runs. Recovery and separation of the products resulted in substantially no alkylated vinylidene chloride.

We claim:

1. A process for the production of alkylated vinylidene chlorides or vinylidene bromides which comprises reacting
   a. at least one of 1,1-dichloroethylene and 1,1-dibromoethylene with
   b. at least one alkylating agent selected from the group consisting of olefins of the formula

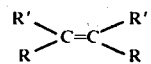

wherein the total number of carbon atoms is 4 to 20, R and R' represent hydrogen or alkyl containing 1 to 12 carbon atoms with the proviso that R is hydrogen if two R' groups together represent an alkylene group containing 3 to 6 carbon atoms, or a cyclo alkylene group containing 5 or 6 carbon atoms or an alkenylene group containing 6 carbon atoms, tert-alkyl halides, and second or tertiary alcohols, in
   c. a reaction medium containing 75–100 weight percent trifluoromethanesulfonic acid and, based on total reaction medium, from 0–25 weight percent water, from 0–25 weight percent methanol, and from 0–10 weight percent BF$_3$.

2. A process according to claim 1 wherein said alkylating agent is a secondary alcohol of the formula:

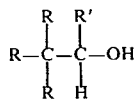

wherein the total number of carbon atoms is 4 to 20, R represents hydrogen or alkyl, and R' alkyl, said alkyls containing 1 to 12 carbon atoms with the proviso that R' and one R group together can represent an alkylene group containing 3 to 8 carbon atoms, cycloalkylene group containing 5 or 6 carbon atoms, or an alkenylene group containing 6 or 7 carbon atoms.

3. A process according to claim 1 wherein said alkylating agent is a tertiary alcohol of the formula:

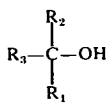

wherein the total number of carbon atoms is 4 to 20, and $R_1$, $R_2$, and $R_3$ can be the same or different and represent alkyl containing 1 to 12 carbon atoms.

4. A process according to claim 1 wherein (c) is (1) trifluoromethanesulfonic acid or (2) aqueous trifluoromethanesulfonic acid or (3) methanol-trifluoroethanesulfonic acid or (4) $BF_3$ in combination with at least one of (1), (2), or (3).

5. A process according to claim 4 wherein the reaction is carried out in liquid $SO_2$ as solvent.

6. A process according to claim 1 wherein said reaction is carried out at a temperature in the range of −40°C to 50°C and the molar ratio of (a) to (b) is in the range of 0.3:1 to 10:1, and the molar ratio of (c) to (a) is in the range of 0.5:1 to 10:1.

7. A process according to claim 1 for the alkylation of vinylidene chloride which comprises reacting vinylidene chloride with an olefin selected from 2-methylbutene-2, isobutylene, pentene-1, cyclohexene, cyclopentene, and norbornene reaction mixture.

8. A process according to claim 1 for the production of 1,1-dichloro-2-(1-bicyclo-[3.3.0]-octyl)ethylene which comprises reacting vinylidene chloride with 1,5-cyclooctadiene in aqueous trifluoromethanesulfonic acid containing $BF_3$.

9. A process according to claim 1 for the production of cyclohexylvinylidene bromide which comprises reacting vinylidene bromide with cyclohexene in a reaction medium of methanol-trifluoromethane-sulfonic acid containing $BF_3$.

10. A process according to claim 1 for the alkylation of vinylidene chloride which comprises reacting vinylidene chloride with cyclohexene in trifluoromethanesulfonic acid and liquid $SO_2$ solvent.

11. A novel compound which is 1,1-dichloro-2-(1-bicyclo-[3.3.0]octyl)ethylene.

12. A process according to claim 1 wherein (c) is trifluoromethanesulfonic acid alone or trifluoromethanesulfonic acid and at least one of water, methanol, and $BF_3$, and wherein, based on total reaction medium, the amount of water present ranges up to 10 weight percent, the amount of methanol present ranges up to 10 weight percent, and the amount of $BF_3$ present ranges from 6–8 weight percent.

\* \* \* \* \*